United States Patent [19]

Ito

[11] Patent Number: 4,807,593
[45] Date of Patent: Feb. 28, 1989

[54] ENDOSCOPE GUIDE TUBE

[75] Inventor: Hideo Ito, Tokyo, Japan

[73] Assignee: Olympus Optical Co. Ltd., Tokyo, Japan

[21] Appl. No.: 47,855

[22] Filed: May 8, 1987

[51] Int. Cl.⁴ .............................................. A61B 1/00
[52] U.S. Cl. ...................................................... 128/4
[58] Field of Search ..................... 128/3, 4, 5, 6, 7, 11

[56] References Cited

U.S. PATENT DOCUMENTS 2,797,683  7/1957  Aiken ...................................... 128/6
3,032,031  5/1962  Moore ..................................... 128/6
4,567,882  2/1986  Heller ..................................... 128/11

FOREIGN PATENT DOCUMENTS 57-42801  3/1982  Japan .

Primary Examiner—William H. Grieb
Attorney, Agent, or Firm—Ladas & Parry

[57] ABSTRACT

The endoscope guide tube comprises a flexible hollow cylinder to be inserted into a body cavity so as to guide the distal end portion of the flexible tube of an endoscope into the body cavity, an opening formed in the peripheral wall of the hollow cylinder, and an instrument-guiding passage provided in the hollow cylinder and extending along the longitudinal axis of the hollow cylinder from the proximal end of the hollow cylinder to a position close to the opening.

11 Claims, 5 Drawing Sheets

ENDOSCOPE GUIDE TUBE

BACKGROUND OF THE INVENTION

The present invention relates to a guide tube to be inserted into a body cavity so as to smoothly guide the distal end portion of the flexible tube of an endoscope into the body cavity.

A guide tube of this type is disclosed in Japanese Utility Model Disclosure No. 57-42801. The tube comprises a flexible hollow cylinder to be inserted into a body cavity for inserting the distal end portion of the flexible tube of an endoscope the into a body cavity. The guide tube is used for two purposes. First, it is used to insert the distal end portion of an endoscope into a body cavity, thereby smoothly and repeatedly to reduce the patients suffering from the repeated insertions of the distal end portion into the body cavity. Secondly, it is used to suppress bending of the distal end portion due to reaction with the inner wall of the body cavity.

The guide tube cannot prevent, however, that part of the distal end portion which protrudes from the guide tube into the body cavity from being moved by peristaltic movement of the inner wall of the body cavity. This results in the following problem. When an endoscope is used to treat an affected tubercle within a body cavity, such as a polyp or a varix, an instrument such as a minute forceps is inserted into the body cavity via a channel provided in t he distal end portion of the endoscope. The instrument is guided to the tubercle. Then, the unit for operating the instrument, located at the proximal end of the flexible tube, is operated, thereby operating the instrument. That part of the distal end portion which extends from the guide tube is very likely to move due to the peristalitic movement of the inner wall of the body cavity. The affected tubercle also moves due to this peristaltic movement. Therefore, a great skill is required to operate the instrument-operating unit in order to move the instrument to the tubercle an drive it properly. As a result, nobody but a doctor who is skilled and much experienced in operating endoscopes can treat a affected tubercle within body cavity.

SUMMARY OF THE INVENTION

It is accordingly the object of this invention to provide an endoscope guide tube which enables a doctor to successfully treat an affected tubercle within a body cavity, such as a polyp or a varix, even if the doctor is not so skilled or experienced in operating the instrument and/or the endoscope.

To accomplish this object, according to the present invention, there is provided an endoscope guide tube comprising a flexible hollow cylinder to be inserted into a body cavity, into which the distal end portion of the flexible tube of an endoscope is inserted so as to be guided into the body cavity. An opening formed in the peripheral wall of the hollow cylinder. An instrument-guiding passage is mounted on the inner peripheral surface of the hollow cylinder so as to extend along the longitudinal axis of the hollow cylinder from the proximal end of the hollow cylinder to a position close to the opening.

This endoscope guide tube of
is inserted into the body cavity until a tubercle in the body cavity which is to be treated is caught in the opening. Then, the distal end portion of the flexible tube of an endoscope is inserted into the hollow cylinder until its distal end comes close to the tubercle. Finally, the instrument for treating the tubercle is inserted through the instrument-guiding passage of the guide tube, not through any channel provided in the flexible tube of the endoscope. Once the tubercle is caught in the opening, it can no longer move despite the peristaltic movement of the inner wall of the body cavity. Since the distal end portion of the flexible tube is too, located in the hollow cylinder, it is neither bent nor moved by the peristaltically moving inner wall of the body cavity, either. Further, since the instrument is inserted in the passage, the channel provided in the flexible tube, which is otherwise be used to guide this instrument, can used to guide another instrument to the tubercle, and the tubercle can thus be treated easily and quickly.

In brief, the guide tube of the invention can prevent both the affected tubercle and the distal end of the flexible tube of the endoscope from moving in spite of peristaltic movement of the inner wall of the body cavity. The endoscope guide tube makes it easier for a doctor who is not so experienced in operating endoscopes to successfully treat an affected tubercle found in a body cavity.

DETAILED DESCRIPTION OF THE PREFERRED EMBODIMENTS

Figure 1:
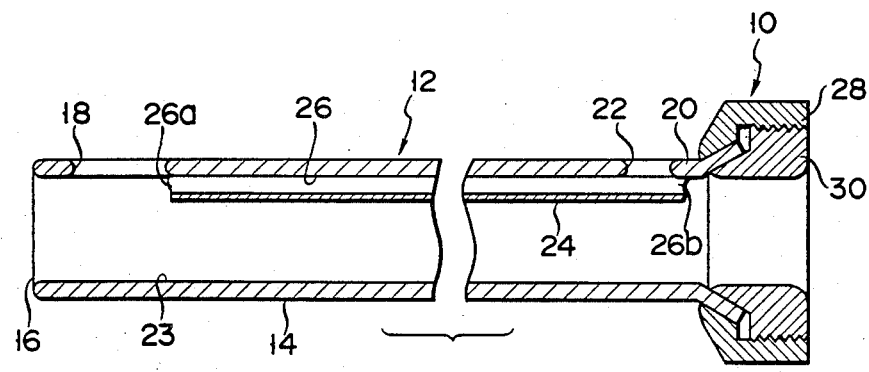
FIG. 1 is a schematic longitudinal, sectional view of an endoscope guide tube according to a first embodiment of the present invention, taken along line I—I in FIG. 2.
Figure 2:
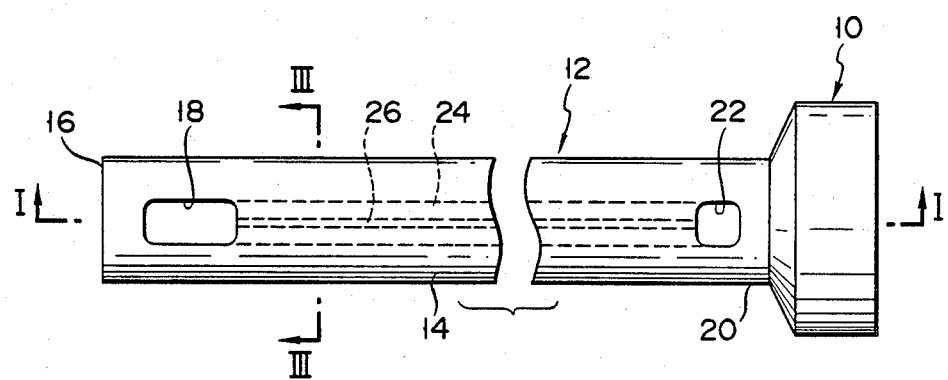
FIG. 2 is a plan view schematic showing the endoscope guide tube shown in FIG. 1.
Figure 3:
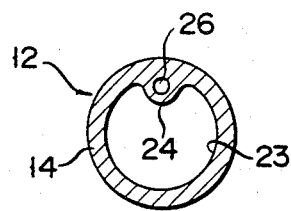
FIG. 3 is a schematically cross-sectional view of the tube, taken along line III—III in FIG. 2.

FIGS. 1 to 3 show an endoscope guide tube according to a first embodiment of the present invention. As shown in these figures, the guide tube comprises approximal end section 10 and an insertion section 12. Section 12 is a transparent, flexible hollow cylinder 14, made for example, of polyurethane resin. A first opening 18 is formed in a distal end portion 16 of the peripheral wall of cylinder 14. Opening 18 is rectangular, is about 30 mm long and about 7 mm wide, extends along the longitudinal axis of hollow cylinder 14, and four has rounded edges. A second opening 22 is formed in a proximal end portion 20 of cylinder 14. This opening 22 is square-shaped with its four edges rounded. As shown in FIG. 3, a half-round bar 24 is provided on the inner peripheral surface of the peripheral wall of hollow cylinder 14 integrally with the hollow cylinder 14. Bar 24 extends along the longitudinal axis thereof between the rear edge of first opening 18 and the rear edge of second opening 22. An instrument-guiding passage 26 is formed in bar 24 which opens at its opposite ends 26a and 26b into the first opening 18 and second opening 22. Proximal end section 10 comprises an outer ring 28 and inner ring 30. Inner ring 30 is in screw engagement with outer ring 28, releasably clamping the proximal end 20 of hollow cylinder 14.

Figure 4:
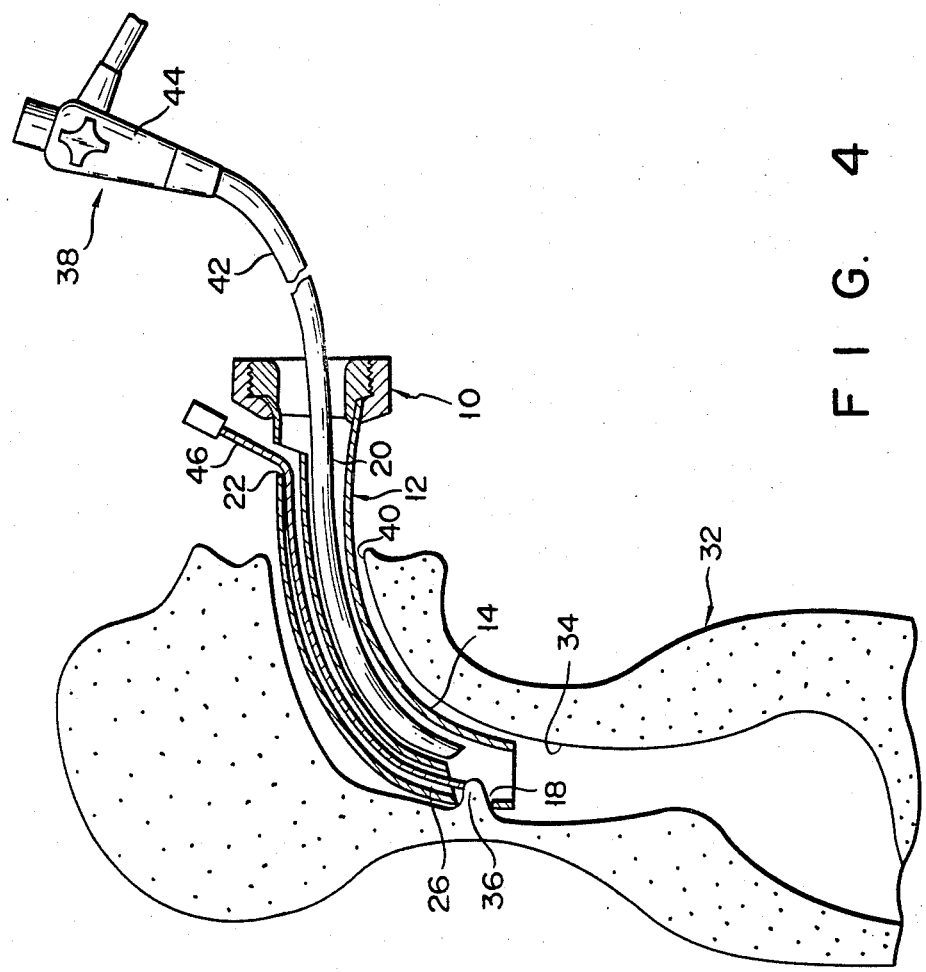
FIG. 4 is a diagram showing the guide tube of FIG. 1 inserted from a patient's mouth to his or her esophagus, and showing how the guide tube guides the distal end of the flexible tube of an endoscope to an affected tubercle protruding from the inner wall of the esophagus.

FIG. 4 shows how the endoscope guide tube shown in FIGS. 1 to 3 is used. Assume that patient 32 has a tubercle 36, such as a varix, protruding from the inner surface of the esophagus 34. In order to treat tubercle 36, while observing tubercle 36 through endoscope 38, the doctor inserts insertion section 12 from the patient's mouth 40 to his or her esophagus 34. Then, he or she inserts the flexible tube 42 of endoscope 38 through inner ring 30 into inner hole 23 of insertion section 12. Next, the doctor operates the operation section 44 of endoscope 38 until the distal end of flexible tube 42, in which an objective lens is provided, reaches and faces tubercle 36. In other words, the doctor operates section 44 until he or she finds tubercle 36. Then, he or she pinches proximal end section 10, and pushes or pulls and rotates insertion section 12 until tubercle 36 is caught in first opening 18 of insertion section 12. This successfully done, the doctor inserts a thin flexible treatment member 46, such as an injection needle, into instrument-guiding passage 26 through second opening 22. The doctor inserts treatment member 46 further through passage 26, while observing tubercle 36 caught in first opening 18 through endoscope 38, thereby thrusting the treatment member 46 (injection needle) into tubercle 36. Then, he or she injects tissue-hardening liquid into tubercle 36, thereby hardening this tubercle 36.

Figure 5:
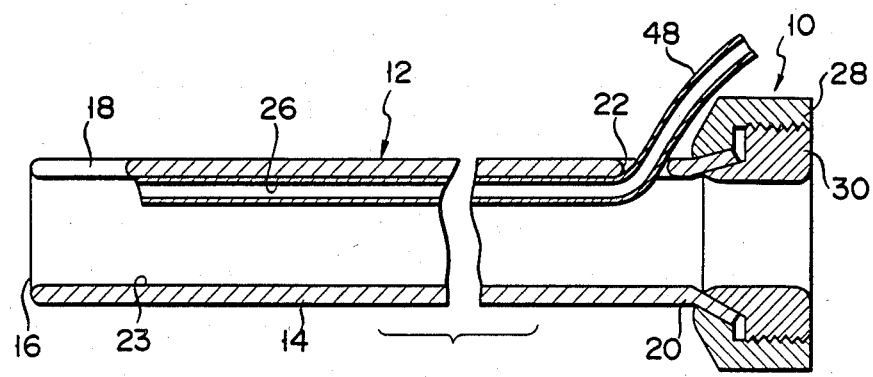
FIG. 5 is a schematic longitudinal, sectional view of an endoscope guide tube according to a second embodiment of the present invention, taken along line V—V in FIG. 6.
Figure 6:
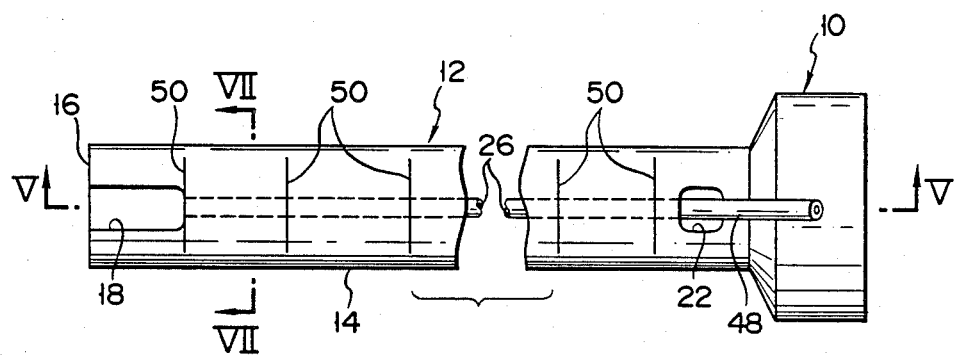
FIG. 6 is a plan view schematically showing the endoscope guide tube shown in FIG. 5.
Figure 7:
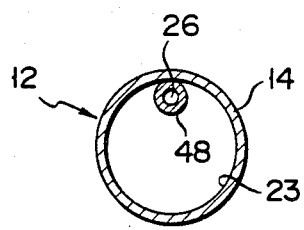
FIG. 7 is a cross-sectional view of the guide tube of FIG. 5, taken along line VII—VII in FIG. 6.

FIGS. 5 to 7 show an endoscope guide tube according to a second embodiment of the invention. Those the components this embodiment which are identical to those of the guide tubes of the first embodiment are designated by the same numerals in these figures, and will not be described in detail.

As is shown in FIGS. 5 and 6, the short edge (front edge) of first opening 18, which is located adjacent to the distal end of the hollow cylinder 14, is cut so as to open first opening 18 in the distal end of transparent, hollow cylinder 14. In this embodiment, flexible tube 48 made of transparent material is used to function as an instrument-guiding passage. Tube 48 extends through second opening 22 into hollow cylinder 14 and reaches the rear edge of slit 18'. That portion of tube 48 located within hollow cylinder 14 is adhered or fused to the inner peripheral surface of hollow cylinder 14. Graduation 50 is cut in the outer peripheral surface of hollow cylinder 14, thus indicating the distance from the rear edge of first opening 18. When a doctor has inserted the guide tube of the second embodiment into the patient's esophagus, and has then inserted the flexible tube of an endoscope into the guide tube, in order to stop bleeding, he or she can quickly locate the bleeding region, since the hollow cylinder 14 and tube 48 are transparent. If the doctor has examined the same region before, by using the endoscope, and has measured the distance between the patient's mouth and this region, he or she can more quickly locate this region. Hence, he or she can stop the bleeding within a short time, thus quickly relieving the patient from pain.

Figure 8:
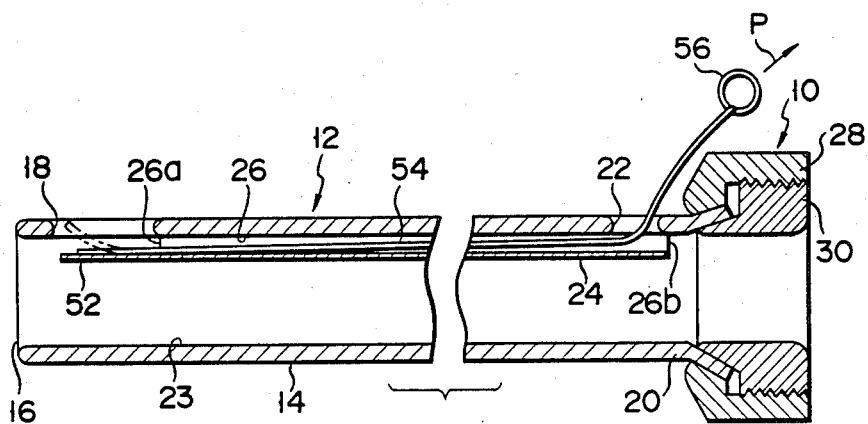
FIG. 8 is a schematic longitudinal, sectional view of an endoscope guide tube according to a third embodiment of the present invention, taken along line VIII—VIII in FIG. 9.
Figure 9:
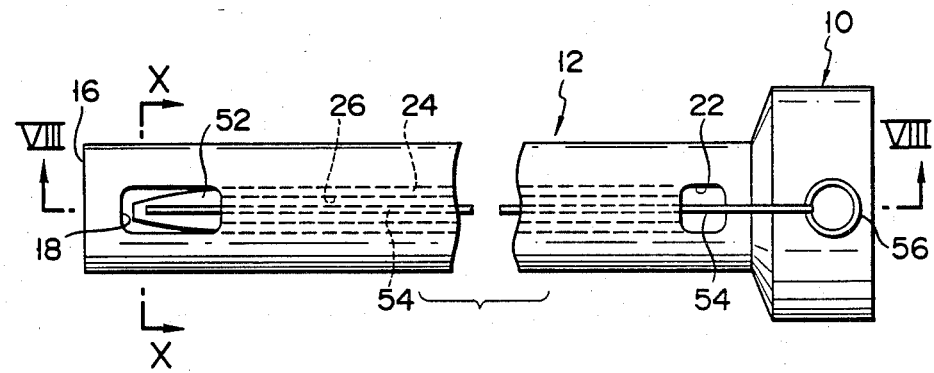
FIG. 9 is a plan view schematically showing the endoscope guide tube shown in FIG. 8.
Figure 10:
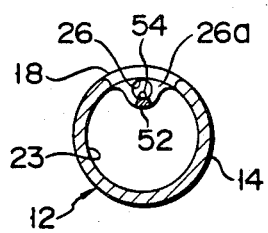
FIG. 10 is a cross-sectional view of the guide tube of FIG. 8, taken along line X—X in FIG. 9.

FIGS. 8 to 10 shows another endoscope guide tube, i.e. a third embodiment of the invention. Those components of this embodiment which are identical to those of the guide tubes of the first embodiment are designated by the same numerals in these figures, and will not be described in detail.

As is shown in FIGS. 8 and 9, half-round bar 24 has a tongue-like member 52 at its distal end aligned with the rear edge of first opening 18. Tongue-like member 52 protrudes from the radially inner end portion of the distal end of half-round bar 24, and extends along the longitudinal axis of cylinder 14. This member 52 is so long that its tip is aligned with the front edge of first opening 18. A wire 54 extends through instrument-guiding passage 26. It is fastened at one end to the tip of tongue-like member 52. Its other end portion extends out of cylinder 14 through second opening 22, and is fastened to a ring 56 provided outside cylinder 14. When ring 56 is moved in the direction of arrow P (FIG. 8), tongue-like member 52 is bent upward and pulled into first opening 18, as is indicated by the two-dot, one-dash lines. When member 52 is bent in this way, the distal end of any instrument inserted through the patient's mouth into instrument-guiding passage 26 can be readily guided to an affected tubercle found in the esophagus.

Figure 11:
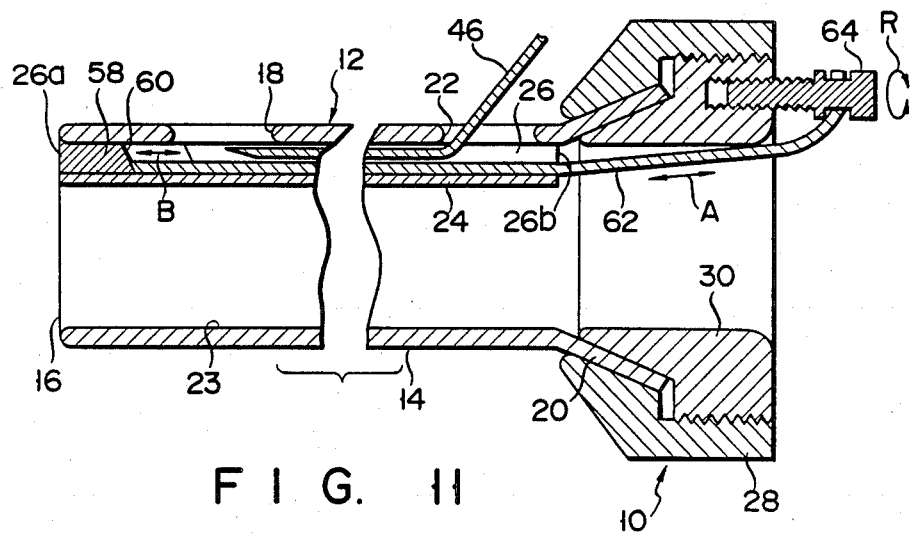
FIG. 11 is a longitudinal, sectional view schematically showing an endoscope guide tube according to a fourth embodiment of the present invention.

FIG. 11 shows yet another endoscope guide tube, i.e., a fourth embodiment of the present invention. Those components of this embodiment which are identical to those of the guide tubes of the first embodiment are designated by the same numerals in FIG. 11, and will not be described in detail.

In this embodiment, half-round bar 24 extends from the rear edge of first opening 18 to the distal end 16 of cylinder 14. A slider 58 is slidably provided within instrument-guiding passage 26 between first opening 18 and the distal end of cylinder 14. Slider 58 has a tapered rear end 60 inclined toward the distal end of cylinder 14. A cable 62 is fastened at one end to this tapered end 60 of slider 58. Its other end portion extends out of the guide tube through inner ring 30 and is connected to screw 64 threaded in a screw hole cut in the outer end surface of inner ring 30. When screw 64 is rotated in one direction or the other, shown by arrow R (FIG. 11), cable 62 is moved along the longitudinal axis of cylinder 14 as is shown by arrow A, thereby moving slider 58 in the same direction as is shown by arrow B. When slider 58 is moved such that its tapered end 60 moves to first opening 18, tapered end 60 can guide the tip of an instrument 46 (e.g., an injection needle), which has been inserted through instrumentguiding passage 26, from cylinder 14 through first opening 26. Slider 58, cable 62, screw 64 cooperate to enable the doctor to readily operate instrument 46.

Figure 12:
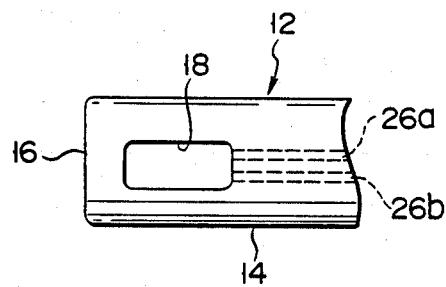
FIG. 12 is a plan view schematically showing part of an endoscope guide tube according to a fifth embodiment of the present invention.
Figure 13:
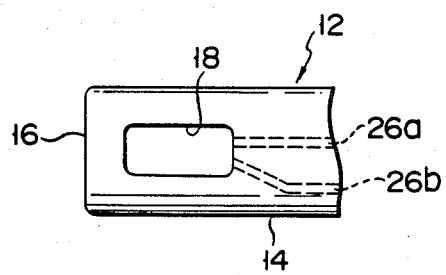
FIG. 13 is a plan view schematically showing part of an endoscope guide tube according to a sixth embodiment of this invention.

FIGS. 12 and 13 show the distal end portions of two other endoscope guide tubes, i.e., fifth and sixth embodiments of the invention. Those components of this embodiment which are identical to those of the guide tubes of the first embodiment are designated by the same numerals in these figures, and will not be described in detail.

In the fifth embodiment (FIG. 12), two parallel instrument-guiding passages 26a and 26b are formed in half-round bar 24 integrally formed with hollow cylinder 14 and are open to first opening 18 cut in cylinder 14. In the sixth embodiment (FIG. 13), two instrument-guiding passage 26a and 26b are formed in half-round bar 24, which is integrally formed with cylinder 14, and are open to first opening 18 cut in cylinder 14. Passage 26b is parallel to passage 26a, except for the distal end portion which is inclined such that the instruments inserted and guided through these passages 26a and 26b intersect in first opening 18. When a doctor uses either the fifth embodiment or the sixth embodiment, he or she can use two medical instruments at the same time, thereby treating an affected tubercle in a shorter time. In particular, when he or she uses the sixth embodiment, he or she can readily and correctly treat an affected tubercle caught in first opening 18 since the two instruments intersect with each other in first opening 18.

Needless to say, the present invention is not limited to the embodiments described above. Various changes and modifications can be made within the spirit and scope of the invention.

What is claimed is:

1. An endoscope guide tube comprising:
    a flexible hollow cylinder to be inserted into a body cavity so as to guide the distal end portion of the flexible tube of an endoscope into the body cavity, said hollow cylinder having an opening which is formed in the peripheral wall of said hollow cylinder, and an instrument-guiding passage which is provided in said hollow cylinder to extend along the longitudinal axis of said hollow cylinder from the proximal end of said hollow cylinder to said opening and is opened at its extended end toward the opening; and
    a proximal-end holding section having an outer and an inner ring, which is so arranged as to clamp said proximal end of said hollow cylinder in the radial direction of the hollow cylinder.

2. The endoscope guide tube according to claim 1, wherein an elongated member is formed on the inner peripheral surface of said hollow cylinder and extends along the longitudinal axis of said hollow cylinder from the proximal end of said hollow cylinder to said position near said opening, and said instrument-guiding passage is formed in said elongated member.

3. The endoscope guide tube according to claim 1, wherein said opening is cut in the distal end of said hollow cylinder.

4. The endoscope guide tube according to claim 1, wherein an opening is formed in the proximal end portion of said hollow cylinder and communicates with said instrument-guiding passage.

5. The endoscope guide tube according to claim 1, wherein a thin tube is provided on the inner peripheral surface of said hollow cylinder and extends from the proximal end of said hollow cylinder to a position close to said opening and said instrument-guiding passage is the hole of the thin tube.

6. The endoscope guide tube according to claim 1, wherein said hollow cylinder is made of transparent material, and graduation is formed on the outer peripheral surface of said hollow cylinder in the longitudinal direction of said hollow cylinder.

7. The endoscope guide tube according to claim 1, further comprising another instrument-guiding passage provided in said hollow cylinder and extending along the longitudinal axis of the hollow cylinder from the proximal end of the hollow cylinder to a position close to the opening.

8. An endoscope guide tube, comprising:
    a flexible hollow cylinder to be inserted into a body cavity so as to guide the distal end portion of the flexible tube of an endoscope into the body cavity;
    an opening formed in the peripheral wall of said hollow cylinder;
    an elongated instrument-guiding passage provided in said hollow cylinder to extend along the longitudinal axis of said hollow cylinder from the proximal end of the said hollow cylinder to said opening and opened at its extended end toward said opening;
    an elongated member formed on the inner peripheral surface of said hollow cylinder and extending along said longitudinal axis of said hollow cylinder from said proximal end of said hollow cylinder to a position close to said opening;
    a tongue-like member extending from that end of said elongated member which is close to said opening, and is located below said opening; and
    a cable extending through said instrument-guiding passage and fastened at one end to said tongue-like member.

9. An endoscope guide tube, comprising:
    a flexible hollow cylinder to be inserted into a body cavity so as to guide the distal end portion of the flexible tube of an endoscope into the body cavity;
    an opening formed in the peripheral wall of said hollow cylinder;
    an elongated instrument-guiding passage provided in said hollow cylinder to extend along the longitudinal axis of said hollow cylinder from the proximal end of said hollow cylinder to said opening and opened at its extended end toward said opening;
    another instrument-guiding passage provided in said hollow cylinder and extending along said longitudinal axis of said hollow cylinder from said proximal end of said hollow cylinder to a position close to the opening;
    said other instrument-guiding passage having a distal end portion with another longitudinal axis intersects with said longitudinal axis of said instrument-guide passage.

10. An endoscope guide tube comprising:
    a flexible hollow cylinder to be inserted into a body cavity so as to guide the distal end portion of the flexible tube of an endoscope into the body cavity;
    an opening formed in the peripheral wall of the hollow cylinder; and
    an instrument-guiding passage provided in the hollow cylinder and extending along the longitudinal axis of the hollow cylinder from the proximal end of the hollow cylinder to the distal end of the hollow cylinder, the opening being set apart from the distal end of said hollow cylinder;

a slider slidably in the instrument-guiding passage between the distal end of the hollow cylinder and a front edge of the opening; and a cable extending through the instrument-guiding passage and fastened at one end to the slider.

11. An endoscope guide tube, comprising:

a flexible, longitudinally hollow cylinder having a longitudinal peripheral wall between a proximal and a distal end of the hollow cylinder for insertion into a body cavity;

an opening through the peripheral wall radially of the hollow cylinder proximate the distal end of the hollow cylinder;

an instrument-guiding passage in the peripheral wall from one end at the proximal end of the hollow cylinder to an opposite end at the opening, the ends of the passage being open; and a proximal-end holding section having outer and inner ring means for releasably clamping the proximal end of the hollow cylinder in the radial direction of the hollow cylinder.

* * * * *